United States Patent [19]
Zavislan

[11] Patent Number: 5,836,877
[45] Date of Patent: Nov. 17, 1998

[54] SYSTEM FOR FACILITATING PATHOLOGICAL EXAMINATION OF A LESION IN TISSUE

[75] Inventor: James M. Zavislan, Pittsford, N.Y.

[73] Assignee: Lucid Inc, Henrietta, N.Y.

[21] Appl. No.: 805,045

[22] Filed: Feb. 24, 1997

[51] Int. Cl.$^6$ ...................................................... A61B 5/00
[52] U.S. Cl. .......................... 600/407; 128/922; 382/128; 348/77; 348/79
[58] Field of Search ..................................... 600/407, 408; 128/920, 922; 382/128, 131, 132, 190, 195; 348/46, 68, 73, 77, 79; 356/379

[56] References Cited

U.S. PATENT DOCUMENTS

| | | |
|---|---|---|
| 4,693,255 | 9/1987 | Beall . |
| 4,752,879 | 6/1988 | Brunnett . |
| 4,856,528 | 8/1989 | Yang et al. . |
| 4,860,112 | 8/1989 | Nichols et al. . |
| 4,945,410 | 7/1990 | Walling . |
| 5,005,126 | 4/1991 | Haskin . |
| 5,034,613 | 7/1991 | Denk et al. . |
| 5,235,510 | 8/1993 | Yamada et al. . |
| 5,260,871 | 11/1993 | Goldberg . |
| 5,359,513 | 10/1994 | Kano et al. . |
| 5,374,965 | 12/1994 | Kanno . |
| 5,434,611 | 7/1995 | Tamura . |
| 5,441,047 | 8/1995 | David et al. . |
| 5,544,649 | 8/1996 | David et al. . |

OTHER PUBLICATIONS

Optical characterization of dense tissues using low–coherence interferometry, SPIE vol. 1889,pp. 197–211 (1993).
Ackerman's Surgical Pathology, Mosby Eighth Edition, vol. Two, Appendix I, Appendix A, Appendix H.
Lasers & Optronics, LAB Notes, Jan. 1997.

*Primary Examiner*—Marvin M. Lateef
*Assistant Examiner*—Shawna J. Shaw
*Attorney, Agent, or Firm*—K. Lukacher; M. Lukacher

[57] ABSTRACT

In order to facilitate pathological examination of a lesion in in-vivo tissue, a system and method are provided having a computer system in which both a camera for producing a digital macroscopic picture of the lesion and an imager are coupled to the computer system. The imager is responsive to the computer system and has optics for scanning the lesion to generate images representing microscopic sections of the lesion which provide sufficient information for pathological examination of the lesion. The computer system generates location information, referencing the location in the macroscopic picture of the lesion where the lesion was scanned to the images, and stores data in an electronic file structure which contains at least a representation of the images, a representation of the macroscopic picture, and the location information. The file structure may then be sent to another computer system for viewing the images stored in the file structure to facilitate pathological examination of the lesion by persons trained to interpret such images, adding a diagnostic report about the lesion to the data of the file structure, and sending back the file structure to the computer system that originated it.

15 Claims, 5 Drawing Sheets

SYSTEM FOR FACILITATING PATHOLOGICAL EXAMINATION OF A LESION IN TISSUE

DESCRIPTION

The present invention relates to a system (method and apparatus) for facilitating pathological examination of a lesion in tissue, and relates, particularly, to a system for facilitating pathological examination of a lesion in tissue in which the lesion is scanned in order to generate images representing microscopic slices of the lesion.

Traditionally, pathological examination of a lesion in the tissue of a patient requires that a pathologist interpret slides prepared from sections of the lesion, i.e., histologically prepared sections or slices. These sections are taken from a biopsy specimen which surgically removes a portion or the entire lesion. This biopsy specimen is frequently called a tissue ellipse, since often it approximates that shape. The borders of the specimen are referred to as margins and may contain diseased or healthy tissue. After suitable processing, the tissue specimen or slices thereof are embedded in paraffin blocks. Histological sections (usually 5–6 microns thick) are then cut from the tissue slices with a microtome and stained for microscopic examination and interpretation by a pathologist.

Pathologists generally require that the histologically prepared sections from the tissue specimen represent a common suite or set of sections selected to provide information to diagnose the type of pathologic lesion and its extent. This suite of sections generally includes at least one section along the major axis of the tissue ellipse (i.e., along the length of the ellipse), at least one to two sections on each side of the tissue ellipse transversing the major axis, and at least three to four sections from the center of the lesion. The number of slices in the suite increases with the size of the lesion. Typically, the slices are taken perpendicular with respect to a surface of the tissue. A description of the preparation of histological sections is shown, for example, in Appendix H of Ackerman's Surgical Pathology, eighth edition (1996).

The interpretation of the slides of the histologically prepared sections of the lesion is recorded by the pathologist in a diagnostic report. Typically, this report in addition to the diagnostic interpretation of the slides, includes specimen information, descriptions and comments. The recommended content of a surgical pathology report is described in Appendix A of Ackerman's Surgical Pathology, eighth edition (1996). The report is forwarded to the physician treating the patient and/or the physician who provided the biopsy to the pathologist.

The paraffin blocks containing the tissue left after preparing the histological sections, the slides, and the diagnostic report together represent an archival record of the pathologist's examination of the lesion. Not all parts of the archival record may be located at the same location, but are cross-referenced to each other. This archival record is retained, in case the pathological examination of the lesion ever needs to be reviewed, for at least a minimum retention time in compliance with regulatory requirements.

Confocal microscopes for scanning tissue can produce microscopic images of tissue sections. Such microscopic image sections may be made in-vivo in tissue without requiring a biopsy specimen of the lesion. Examples of confocal scanning microscopes are found in U.S. patent application Ser. No. 80/650,684, filed May 20, 1996, and Ser. No. 60/025,076, filed Oct. 10, 1996, both by James M. Zavislan, and in Milind Rajadhyaksha et al., "In vivo Confocal Scanning Laser Microscopy of Human Skin: Melanin provides strong contrast," The Journal of Investigative Dermatology, Volume 104, No. 6, June 1995, pages 1–7. For further information concerning the system of the Zavislan applications, see Milind Rajadhyaksha and James M. Zavislan, "Confocal laser microscope images tissue in vivo," Laser Focus World, February 1997, pages 119–127. These systems have confocal optics which direct light to the patient's tissue and image the returned reflected light. Further, microscopic images of tissue sections can be produced by optical coherence tomography or interferometry, such as described in Schmitt et al., "Optical characterization of disease tissues using low-coherence interferometry," Proc. of SPIE, Volume 1889 (1993).

It is a feature of the present invention to generate confocal images representing microscopic sections of a lesion to provide information traditionally available to a pathologist by viewing, under a microscope, slides of a suite of histologically prepared sections of a lesion, and also to enable the storage of such confocal images and their transfer from one location to a pathologist at a remote location for their interpretation.

It is another feature of the present invention to facilitate the pathological examination of lesions especially where images of microscopic sections are obtained electronically and under computer control, which provides for the transmission of such electronic images in a coordinated manner providing more pathological information and enabling such information to be communicated telepathologically to various selected locations. The system of the present invention is therefore more effective in medical imaging than other similar systems heretofore proposed in other areas of medicine, for example, U.S. Pat. No. 4,860,112, issued to Nichols et al., describes a teleradiology system for transmitting scanned x-ray images to various locations. U.S. Pat. No. 5,005,126, issued to Haskin, describes a system for transferring diagnostic image information picked off from the internal analog video signal of imaging equipment, such as a CAT scanner or MRI. U.S. Pat. No. 4,945,410, issued to Walling, describes a satellite communication system for transmitting medical images, produced using a high resolution camera taking a video picture of a photograph, such as an x-ray, from remote satellite locations to a central headquarters, and also for sending back diagnostic analysis to the remote stations.

An object of the present invention is to provide an improved system for facilitating pathological examination of a lesion in tissue in which the lesion is optically scanned to generate images representing a suite of microscopic sections traditionally viewed by a pathologist for examination of a lesion.

Another object of the present invention is to provide an improved system for facilitating pathological examination of a lesion in which an electronic file structure is generated which contains at least images of microscopic sections of the lesion, a macroscopic picture of the lesion, and information referencing the location in the macroscopic picture where the images were scanned.

A further object of the present invention is to provide an improved system for facilitating pathological examination of a lesion in tissue in which the electronic file structure may be sent from a first location, where the data comprising the electronic file was generated, to a second location, where pathological examination of the lesion responsive to the data in the electronic file structure is performed.

A still further object of the present invention is to provide an improved system and method for facilitating pathological examination of a lesion in tissue in which the electronic file structure may further include data representing a diagnostic report about the pathological examination of the lesion, and such file structure may be sent to both the physician treating the patient having the lesion and to archival storage as a document.

Briefly described, the present invention may be embodied in a system for facilitating pathological examination of a lesion located in tissue. The system uses a computer system in which both a camera for producing a digital macroscopic picture of the lesion and an imager are coupled to the computer system. The imager is responsive to the computer system and has optics for generating images representing microscopic sections of the lesion which provide sufficient information for pathological examination of the lesion. The computer system generates location information referencing the location in the macroscopic picture of the lesion to the sections, and stores data in an electronic file structure which contains data representing the images, a representation of the macroscopic picture, and the location information.

Alternatively, the camera may be removed from the system and instead an imager is used which operates in one mode for producing a digital macroscopic picture of the lesion, and in another mode for generating images representing microscopic sections of the lesion.

A system embodying the present invention may further include first and second computer systems at first and second locations, respectively. The computer system briefly described above may be used on as the first computer system. The electronic file structure may be sent from the first computer system to the second computer system over a communication interface (or via soft copy on a diskette). The second computer system receives and stores the electronic file structure, and provides a display for viewing images responsive to the data stored in the electronic file structure to assist in the pathological examination of the lesion. Further, the second computer system may provide for the adding of a diagnostic report about the pathological examination to the data in the electronic file structure, and for sending the electronic file structure to the first computer system.

The system may operate in a real-time mode for sending a single file structure to the second computer system, or the system may operate in a batch mode in which the second computer system receives multiple file structures in a batch and later processes each received file structure.

The term "tissue" as used herein is generic to any body tissue of a patient which has a natural or surgically exposed surface.

The foregoing objects, features and advantages of the invention will become more apparent from a reading of the following description in connection with the accompanying drawings, in which.

Figure 1:
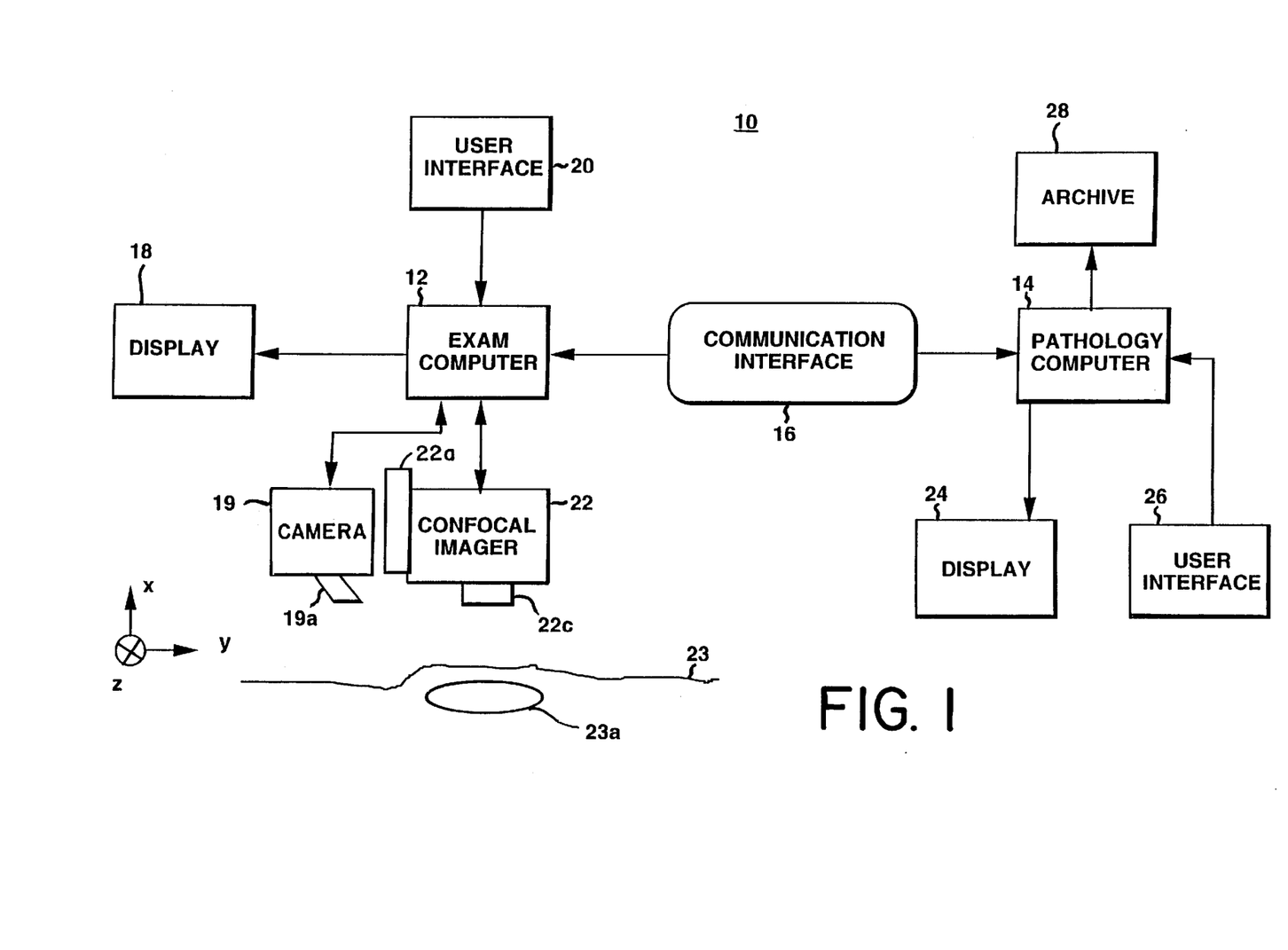
FIG. 1 is a block diagram of a system in accordance with the present invention.

Referring to FIG. 1, a system 10 of the present invention is shown having an exam computer 12. Exam computer 12 represents a computer system, such as a personal computer, which is programmed to operate in accordance with instructions stored in its memory. Peripheral devices are provided for exam computer 12, including a display screen or monitor 18 and a user interface 20, such as a mouse and keyboard. A digital camera 19 with lens 19a operates responsive to exam computer 12 to provide digital images to the exam computer 12, for example, of a lesion 23a in a tissue 23 of a patient. The tissue may represent any natural or surgically exposed surface of the body of the patent having a lesion therein, such as skin, oral mucosa, cervix, or internal body tissue during surgery.

System 10 also includes a confocal imager 22 coupled to exam computer 12. Confocal imager 22 is described as a confocal head in the above referenced U.S. patent applications. Confocal imager 22 has confocal optics, which includes an objective lens 22c, for scanning tissue to generate confocal images representing sections of the tissue. Under control of exam computer 22, confocal imager 22, via its confocal optics, can scan at different planes through lesion 23a to generate confocal images to exam computer 12 which represent microscopic sections of lesion 23a. Although reference is made hereinafter to a confocal imager 22 in system 10, any other types of imager with sufficient resolution for pathological examination of the lesion and which provides digital images of sections of the lesion may be used. For example, an imager may alternatively be used which employs optical coherence tomography, such as described in Schmitt et al., "Optical characterization of disease tissues using low-coherence interferometry," Proc. of SPIE, Volume 1889 (1993). Other type of imager which may be used alternatively to confocal imager 22 is a two-photon laser microscope, such as described in U.S. Pat. No. 5,034,613 to Denk et al., issued Jul. 23, 1991.

Confocal imager 22 includes a translation stage 22a which provides motion of the imager in three orthogonal dimensions (x, y, z), such as on the order of about 15 millimeters in each dimension. Exam computer 12 automatically controls translation stage 22a such that confocal imager 22, i.e., objective lens 22c, is directed to a desired location in tissue 23. Alternatively, translation stage 22a may be manually controlled, such as by a set of micrometers on the stage, to move the confocal imager. Using typical display driving software, exam computer 12 can show images on display 18 provided by camera 19 or confocal imager 22.

Digital camera 19 and confocal imager 22 are in a fixed spatial relationship to each other so that the picture taken by camera 19 corresponds to the area of tissue 23 available to be examined by translating confocal imager 22 on stage 22a. Exam computer 12 can monitor the location of confocal imager 22 with respect to such a picture as the imager moves via translation stage 22a. Digital camera 19 is preferably a color camera which has been calibrated to give accurate color images.

Alternatively, camera 19 may be removed from system 10 when confocal imager 22 provides the picture of the surface of tissue 23. To provide such a picture, confocal imager 22 includes first and second objective lenses which are separately positionable, such as on a turret, in the position of lens 22c. The first objective lens operates at low magnification and does not provide confocal imaging, while the second objective lens operates at a high magnification confocal imaging. Thus, confocal imager 22 in a first macroscopic (low magnification) imaging mode may scan the tissue with the first objective lens to provide a digital picture of the tissue surface to exam computer 12, while in a second confocal imaging mode, the confocal imager scans the tissue through the second objective lens to generate confocal images to exam computer 12 representing microscopic slices. The turret may further include additional objective lens for other levels of magnification with or without confocal imaging to provide confocal images or macroscope pictures at other magnifications as needed.

System 10 further includes at least one pathology computer 14 which can receive and send data from and to exam computer 12 over a communication interface 16. Communication interface 16 may be a cable link between computers 12 and 14, or a connection via a network, such as LAN or Internet. Communication interface 16 may also refer to any means of transferring data between two different computer systems, such as via softcopy on diskette(s), tape, or erasable CD-ROM. Exam computer 12 also can receive and send data from and to pathology computer 14 over communication interface 16.

Pathology computer 14 represents a computer system, such as a personal computer, which is programmed to operate in accordance with instructions stored in its memory. Peripheral devices are provided for pathology computer 14 which include a display screen or monitor 24 and a user interface 26, such as a mouse and keyboard. Pathology computer 14 receives and stores a file structure having files therein from exam computer 12 in its memory. This file structure will be described later in more detail in connection with FIG. 3. Pathology computer 14 allows a user, preferably a trained pathologist, to view on display 24 images from the file structure stored at computer 14, such as confocal images or a picture of the tissue surface, for pathological examination of the tissue represented in such images. Preferably, pathology computer 14 does not allow its user to alter the image data in the stored file structure. Pathology computer 14 may be at a location different from the location of exam computer 12.

Coupled to pathology computer 14 is archive 28 for storage of files from the computer 14. Archive 28 receives and stores data, such as the above file structure, as a document from pathology computer 14 for long-term archival storage. Archive 28 refers to any means capable for long-term storage of files, such as a file server, a hard drive on pathology computer 14, a tape drive, or optical disk. Preferably, archive 28 is off-site from pathology computer 14 and provides permanent data storage of received file structures. Archive 28 may be part of a record-keeping information system for a pathology laboratory, and as such may be similar to record-keeping systems for histological prepared sections of tissue samples, as described in Appendix I of Ackerman's Surgical Pathology, eighth edition (1996).

Figure 2A:
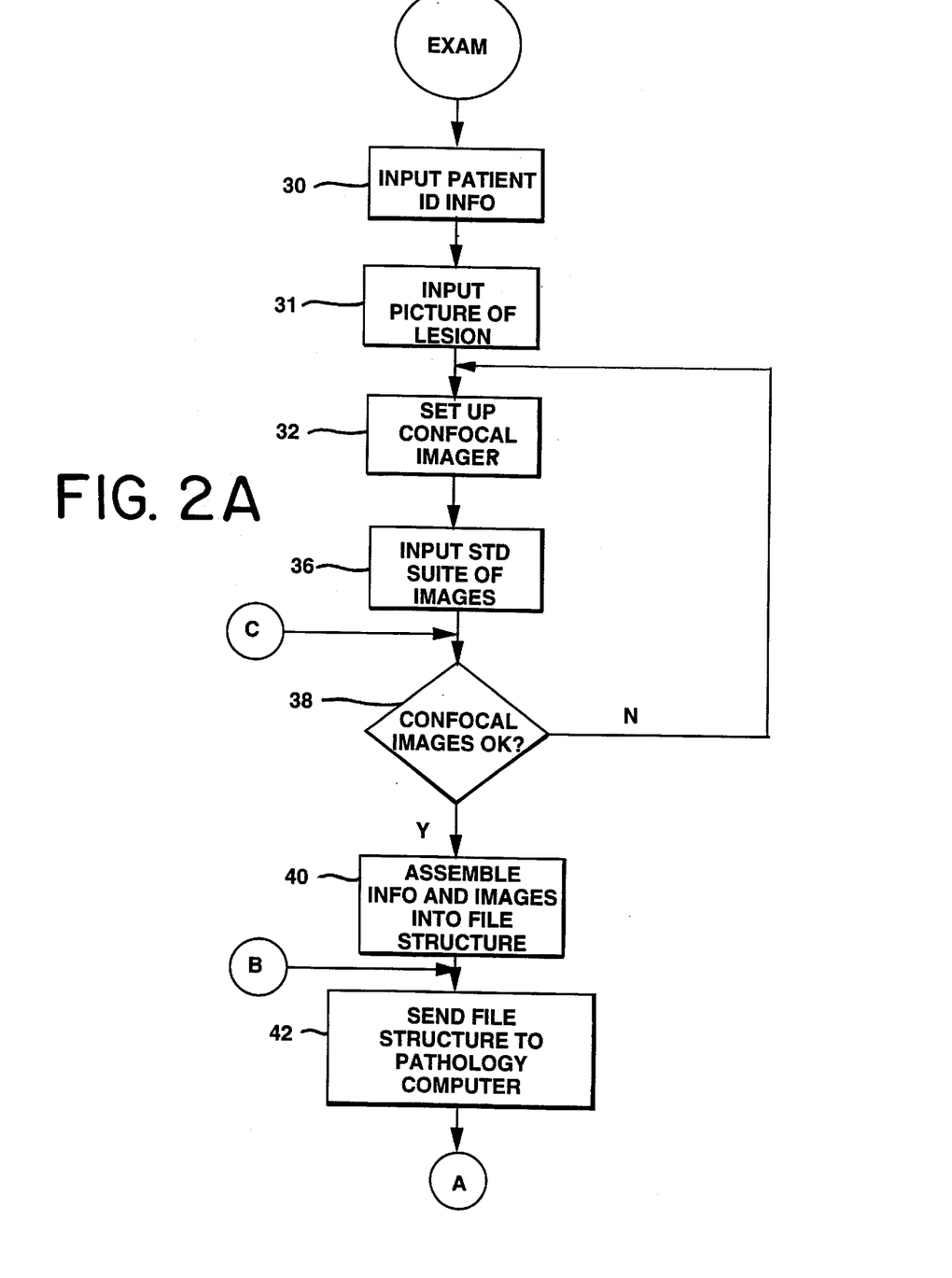
FIGS. 2A and 2B are flow charts showing the operation of the exam computer in the system of FIG. 1.
Figure 2B:
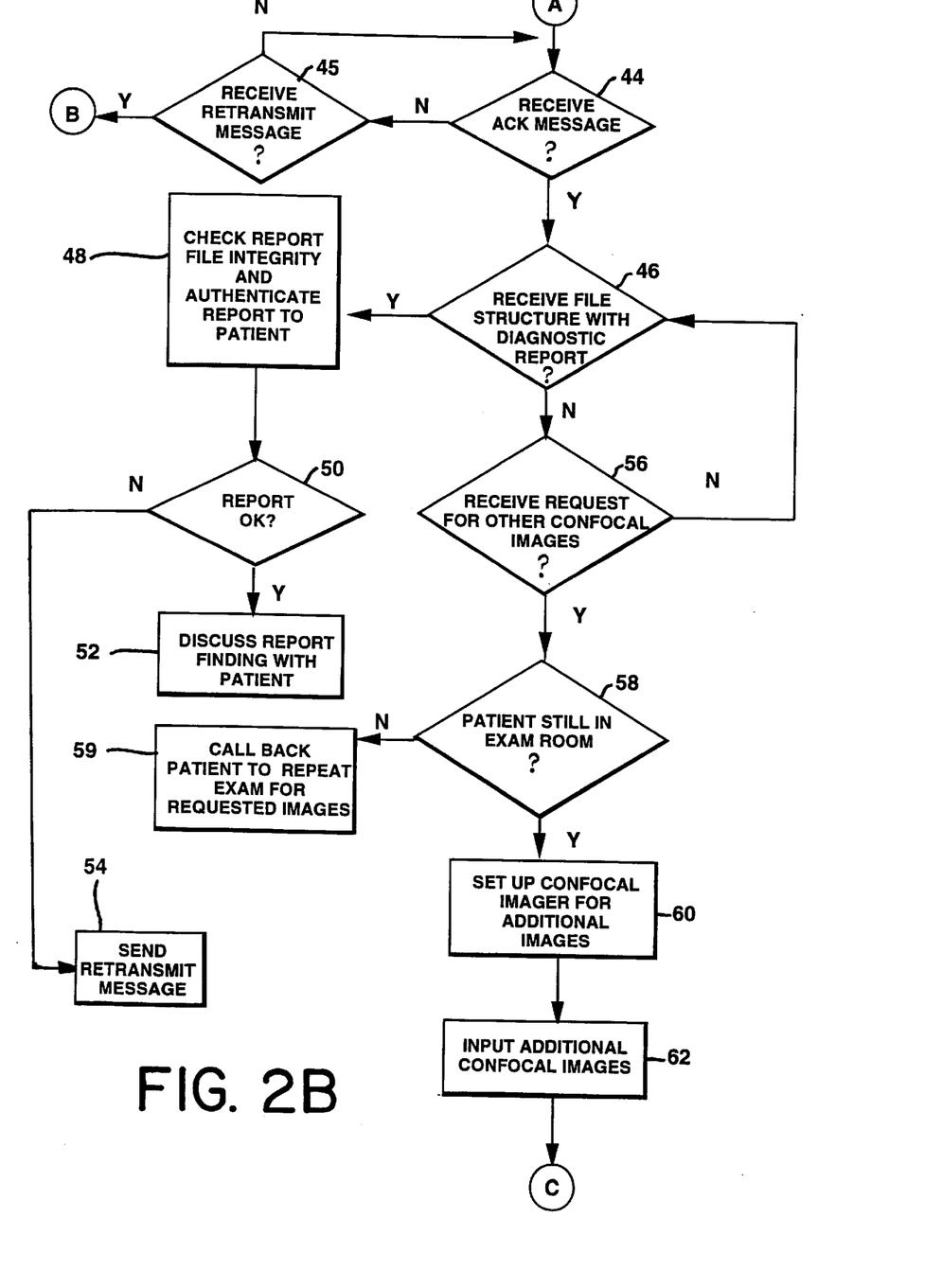

The operation of exam computer 12 is shown in FIGS. 2A and 2B. Labeled circles in the figures represent connecting branches. The user of exam computer 12 first inputs, via user interface 20, patient ID (identification) information for the patient having a lesion or lesions to be pathologically examined (step 30). Patient ID information may include the patient's name, social security number, relevant insurance information, or other similar identifying information. Optionally, the patient ID information may include a picture of the patient's face which may be taken with camera 19 directed to the patient's face. Also, the patient ID file may include information about the pertinent clinical history of the patient relevant to the pathological diagnosis of the lesion, and a gross description of the lesion. This information is provided by the medical personnel, such as the physician treating the patient.

A picture of the lesion is then taken by camera 19 and inputted to exam computer 12 (step 31), or in the alternative, by confocal imager 22 operating in a macroscope imaging mode. This picture is referred to as the macroscopic picture.

At step 32, confocal imager 22 is set up for taking confocal images of different vertical sections (with respect to the surface of tissue 23) through lesion 23a which will include bordering tissue outside of the area of the lesion (step 32). To set up confocal imager 22, the locations in the tissue where each section will be scanned by the confocal imager are selected by exam computer 12 with the assistance of the user. Step 32 may be done by providing exam computer 12 with coordinates in the two-dimensional space of translation stage 22a where the location of each confocal image should be made, as well as the desired depth of the image in the tissue. These coordinates can be determined automatically by exam computer 12 in which the user targets the lesion, such as by the user indicating the size and shape of the lesion relative to the macroscopic picture on display 18 taken with camera 19 (or alternatively, confocal imager 22 operating in a macroscopic imaging mode), as well as the expected depth of the lesion in the tissue. The computer can then automatically determine the location where each vertical confocal image should be made based on the inputted information to provide images sufficient for pathological examination of the lesion. The coordinates can also be determined manually by the user using the macroscopic picture of the lesion on display 18 to select the location where each confocal image should be made and the depth of each image in the tissue.

Based on the set up of confocal imager 22, different sections of the lesion are scanned by the imager to generate a suite (or set) of confocal images representing microscopic sections of the lesion (step 36). The input of this suite of images involves using translation stage 22a by exam computer 12 to automatically position confocal imager 22 at the proper location for each confocal image to be scanned based on the coordinates determined at step 32. In the alternative where translation stage 22a is manually controlled, step 23 would involve orienting confocal imager 22 to lesion 23a, and the user at step 36 would position confocal imager 22 for each confocal image to be scanned using the micrometers of stage 22a. For each confocal image scanned, after either manually or automatically positioning confocal imager 22, the location or coordinates of each confocal image scanned relative to the macroscope picture is stored in memory of exam computer 12. The locations of the confocal images preferably approximate the locations of prior art histologically prepared sections as if the lesion had been a biopsy specimen, such that the information from these confocal images is sufficient for later pathological examination and interpretation. Accordingly, the suite of confocal images is referred to as a standard suite of confocal images, i.e., of imaged sections of the lesion.

The standard suite of confocal images is taken by the confocal imager 22 vertically through the tissue with respect to its surface and preferably includes at least one confocal image along the major axis of the lesion, i.e., the axis which extends along the length of the lesion parallel to the tissue surface, at least one to two confocal images on each side of the lesion transversing the major axis, and at least three to four confocal images from the center of the lesion. Each confocal image of the lesion provides margins on each side having tissue outside of the lesion area. The number of confocal images in the suite increases with the size of the lesion, and preferably adjacent parallel confocal images are spaced at about 0.2 mm to about 1.0 mm from each other. The standard suite of confocal images may optionally include one or more horizontal confocal images through the lesion. Further, if a single confocal image does not have a field of view which encompasses the entire lesion or the region of interest in the tissue, multiple confocal images along the same direction through the lesion may be concatenated in order to provide an imaged section over a large field of view.

The confocal images taken at step 36 are stored in memory of exam computer 12. At step 38, the user may review these images on display 18 to assure that they are OK. If the images are not OK, a no branch is taken to step 32 to repeat steps 32 to 36. If the images are OK, exam computer 12 at step 40 assembles the inputted information and confocal images (i.e., imaged sections of the lesion) into an electronic file structure 80 in its memory, as shown in FIG. 3, and sends file structure 80 over communication interface 16 to pathology computer 14 (step 42) to request pathological examination of the virtual tissue sample defined by the data in file structure 80.

Figure 3:
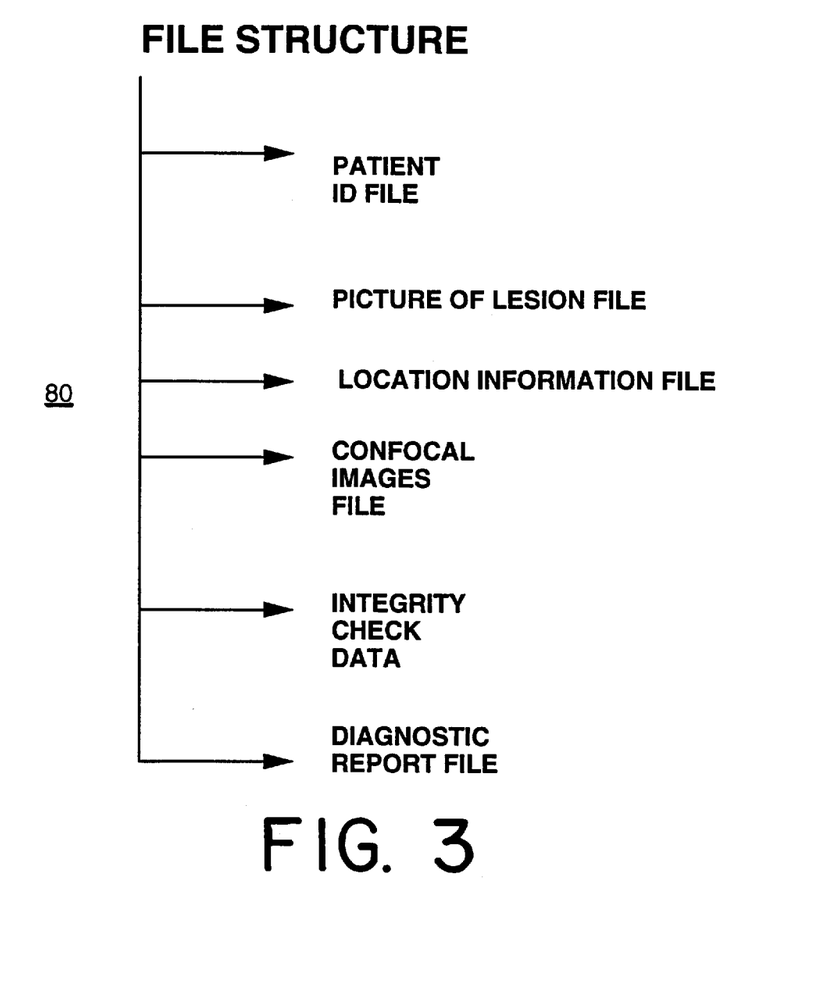
FIG. 3 is a diagram of the electronic file structure used by the system of FIG. 1.

Referring to FIG. 3, the patient ID information inputted at step 30, the macroscopic picture of the lesion inputted at step 31, and the confocal images inputted at step 36 are each stored in a file of file structure 80. Exam computer 12 also assembles and stores in file structure 80 a file having location information referencing the location in the stored macroscopic picture where the different sections of the lesion were scanned by confocal imager 22 to the confocal images. The location information may include the coordinates of the locations for each scanned confocal image taken at step 36, or the location of confocal imager 22 monitored by exam computer 12 for each confocal image. For example, the location information may include information for drawing a line in the stored macroscopic picture of the lesion where each confocal image was scanned, and an identifier to the line which identifies which of the stored confocal images the line is associated with. Optionally, the location information may be incorporated with the stored picture of the lesion in a single file.

Exam computer 12 also assembles and stores into file structure 80 integrity check data for the confocal images stored in the file structure. This integrity check data may be a CHECKSUM value representing the total number of bits of the stored confocal images in file structure 80. File structure 80 further includes a space for a diagnostic report file to be later inputted by the pathologist who interpreted the confocal images stored in the file structure.

Exam computer 12 waits for an acknowledge (ACK) message (step 44) or a retransmit message (step 45) from pathology computer 14. If a retransmit message is received, a branch is taken to step 42 (FIG. 2A) to resend file structure 80. Exam computer 12 waits to receive a file structure with a diagnostic report file from pathology computer 14 (step 46), or a request from pathology computer 14 for other confocal images (step 56), after receiving the ACK message at step 44.

If file structure 80 with a diagnostic report file is received at step 46, the file structure is stored at exam computer 12. The integrity of the report file is then checked and the diagnostic report is authenticated to the patient (step 48) To check the integrity of the report file, a CHECKSUM value which was added by the pathology computer 14 to the integrity check data of file structure 80 is compared to the number of bits in the received diagnosis report file. If the number of bits matches, file integrity of the received report is assured. To authenticate the diagnostic report to the patient, the data in the patient ID file is reviewed to assure that it corresponds to the patient. At step 50, if the report is ok, i.e., authenticated and integrity checked, the physician discusses the report findings with the patient number (step 52), otherwise a message is sent to pathology computer 14. Also, the exam computer 12 may send an acknowledgment message to pathology computer 14 if the report is ok after step 50.

If a request for other confocal images is received by exam computer 12 from pathology computer 14 at step 56, rather than file structure 80 with a diagnostic report file, additional confocal images need to be taken of the lesion. If the patient is not in the exam room, i.e., the room where steps 32–36 was carried out, at the time the request was received (step 58), then the patient must be called back to repeat the exam for the requested images (step 59). However, if the patient is still in the exam room at the time the request was received, then confocal imager 22 is set up for additional requested images (step 60) and the such images are then inputted via confocal imager 22 (step 62). The additional confocal images are then checked if OK (at step 38 of FIG. 2A), and then at step 40 they are assembled with the other stored confocal images in file structure 80 in which both the location information file is updated with the location of the additional confocal images in the stored macroscopic picture of the lesion, and the integrity check data is reset responsive to the additional confocal images stored in the file structure. Steps 44 to 56 are then repeated.

Figure 4:
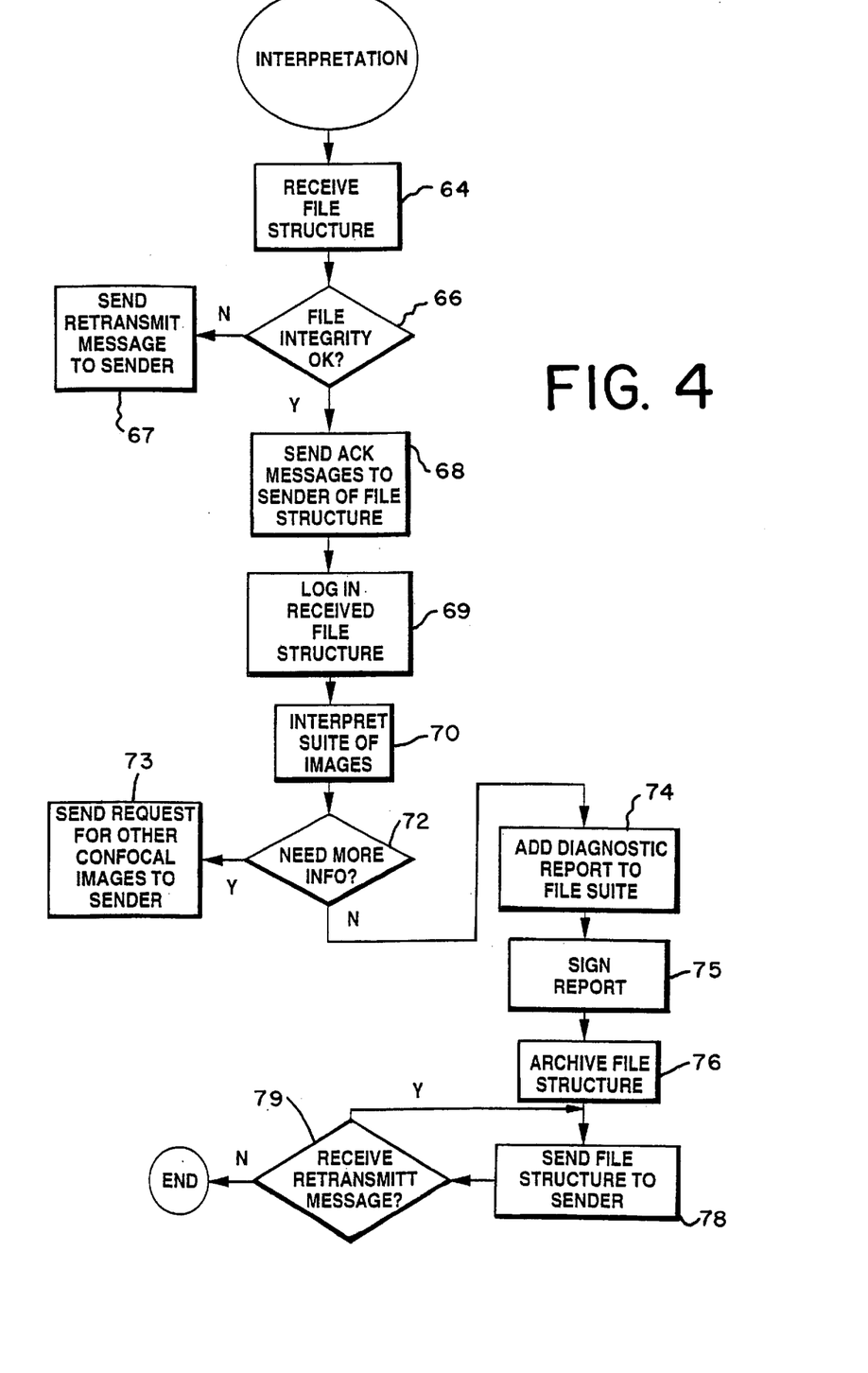
FIG. 4 is a flow chart showing the operation of the pathology computer in the system of FIG. 1.

Referring to FIG. 4, the operation of pathology computer 14 will be described. At step 64, file structure 80 sent from exam computer 12 is received and stored. The file integrity is then checked using the integrity check data of the stored file structure (step 66). This is to assure that after transmission of file structure 80 all the bits of the confocal images are properly received. For example, this may be performed by comparing the CHECKSUM value in integrity check data to the number of bits of the stored confocal images in the file structure. If file integrity is OK, an ACK message is sent to the sender of file structure 80, i.e., exam computer 12 (step 68), otherwise, a retransmit message is sent to the sender (step 67). The integrity check data used by system 10 may in the alternative, or in addition, utilize other error correction code and is not limited to the use of CHECKSUM values.

Next, at pathology computer 14, the received file structure 80 is logged in by assigning a unique surgical pathology number a reference number used for tracking purposes(step 69). The file structure 80 represents a request for pathological examination of the virtual tissue sample defined by the data in the file structure. The surgical pathology number may be automatically, or manually assigned via interface 26. This surgical pathology number is stored in a data field of the diagnostic report file in the stored file structure 80, and preferably, will appear on every page or record of the diagnostic report when prepared.

The pathologist then interprets the confocal images in the stored file structure 80 (step 70) by reviewing on display 24 any relevant information in the patient ID file in the stored file structure 80, such as clinical history, and by viewing on display 24 these images and referencing the images to their location in the macroscopic picture based on the location information in the stored file structure. Preferably, the location information is used by the pathology computer 14 to build an overlay image on a viewed macroscopic picture of the lesion which identifies where each of the confocal images was taken. The pathologist controls the viewing of the confocal images and the macroscopic picture on display 24 via user interface 26, which includes image manipulation such as zoom, rotate, or changing color or contrast. The actual data in the stored file structure received from exam computer 12 cannot be altered by the pathologist. If after viewing the confocal images the pathologist decides that more information is needed in terms of additional confocal images (step 72), a request is sent to the sender for such images at step 73 (this request is received by exam computer 12 at step 56 in FIG. 2B). However, if no additional confocal images are needed, the pathologist adds via user interface 26 a diagnostic report file to file structure 80 having an interpretation of the lesion shown in the confocal images (step 74). This diagnostic report may include text and copies of all or part of any of the images viewed by the pathologist. Such copies in the report may be annotated as desired by the pathologist. The diagnostic report is then signed by the pathologist with his or her digital signature to authenticate that the report was made by that pathologist (step 75). This digital signature may be any mechanism for authentication, such as a personal identification number, password or an electronic representation of the actual signature of the pathologist via a touchpad in user interface 26. The digital signature is preferably stored in a separate data field in the diagnostic report file of file structure 80 reserved for the signature. Also at step 75, after the diagnostic report is signed the pathology computer 14 adds to the integrity check data of file structure 80 another CHECKSUM value representing the number of bits of the diagnostic report file.

In addition to data fields in the diagnostic report file mentioned above, other data fields may be included for example, identification information about the pathology laboratory, such as its name, phone numbers and address.

After the pathologist's signature is stored in the diagnostic report file, the file structure is archived (step 76) by sending a copy of the data in file structure to archive 28 (which maintains the file structure as an archival document), and the file structure is sent to the sender, i.e., exam computer 12, over communication interface 16 (step 78). At step 79, if a retransmit message is received from the exam computer 12, the pathology computer 14 then resends the file structure at step 78. Also, the pathology computer 12 may receive a message from the exam computer 14 acknowledging proper receipt of the file structure sent. If other medical personnel, in addition to the physician treating the patient, require a copy of the diagnostic report, the pathologist may send a copy of the report or the file structure containing the report to such personnel.

Alternatively, step 76 may be carried out after step 75 in which the file structure completed at step 75 is stored at the pathology computer and later archived at such time when file structures are periodically or routinely archived to archive 28. Preferably, the archived file structure represents the authoritative record of the pathological examination so that the integrity of the data may be preserved for later retrieval, if necessary.

System 10 may operate in real-time or batch modes. In real-time mode, file structure 80 once assembled and stored in memory of exam computer 12 soon afterwards is sent to pathology computer 14 at step 42 (FIG. 2A) for real-time interpretation of the imaged lesion. Similarly, after the diagnostic report is prepared, based on the data in a received file structure, and signed, it is sent soon afterwards to exam computer 12 at step 78 (FIG. 4). In batch mode, multiple file structures 80 from several patients are queued, i.e., stored, in memory of exam computer 12 at step 40, and later sent together at step 42 (FIG. 2A) in a batch or sequentially by exam computer 12 over interface 16 to pathology computer 14. Starting at step 64 (FIG. 4), the received file structures are then each later processed at pathology computer 14. Further, file structure 80 once assembled and stored in memory of exam computer 12 may be sent in a batch with other file structures, or singularly, to pathology computer 14 at step 42, and then each received file structure at pathology computer 14 is queued in memory of pathology computer 14 at step 64, or at step 68 (after an acknowledgment message is sent for either an entire batch or each single file structure received). Thereafter, each file structure may be further processed in turn from memory of pathology computer 14 at such time when a pathologist is available. Each file structure, although ready to be sent at step 78 (FIG. 4), may be sent to exam computer 12 either singularly, or in a batch over interface 16.

From the foregoing description, it will be apparent that there has been provided an improved system and method for facilitating pathological examination of a lesion in tissue. Variations and modifications in the herein described system and method in accordance with the invention will undoubted suggest themselves to those skilled in the art. Accordingly, the foregoing description should be taken as illustrative and not in a limiting sense.

What is claimed is:

1. A method for facilitating pathological examination of a lesion located in tissue comprising the steps of:

producing a macroscopic picture of the lesion;

generating images representing microscopic sections of said lesion which provide sufficient information for pathological examination of the lesion;

generating location information referencing the location in said macroscopic picture of the lesion to said sections; and storing data in an electronic file structure which comprises at least a representation of said images, a representation of said macroscopic picture of the lesion, and said location information, wherein said generating step further comprises the step of scanning the lesion with the aid of confocal optics to generate confocal images representing microscopic sections of said lesion.

2. A method for facilitating pathological examination of a lesion located in tissue comprising the steps of:

producing a macroscopic picture of the lesion;

generating images representing microscopic sections of said lesion which provide sufficient information for pathological examination of the lesion;

generating location information referencing the location in said macroscopic picture of the lesion to said sections; and storing data in an electronic file structure which comprises at least a representation of said images, a representation of said macroscopic picture of the lesion, and said location information, wherein said generating step further comprises the step of generating images representing microscopic sections by one of optical coherence tomography, and two-photon laser microscopy.

3. An apparatus for facilitating pathological examination of a lesion located in tissue comprising:

a computer system;

means coupled to said computer system for producing a digital macroscopic picture of the lesion;

an imager coupled to said computer system for generating, responsive to said computer system, images representing microscopic sections of said lesion which provide sufficient information for pathological examination of the lesion; and said computer system further comprises means for generating location information referencing the location in said macroscopic picture of the lesion to said sections, and means for storing data in an electronic file structure which comprises at least a representation of said images, a representation of said macroscopic picture, and said location information, wherein said imager further comprises means for scanning the lesion through confocal optics to generate confocal images representing microscopic sections of said lesion.

4. The method according to claim 1 further comprising the steps of:

performing said producing, generating images, generating location information, and storing steps at a first location;

sending said electronic file structure from said first location to a second location; and receiving and storing said electronic file structure at said second location.

5. The method according to claim 4 further comprising the step of:

performing at said second location a pathological examination of said lesion in accordance with said data in said received electronic file structure.

6. The method according to claim 5 further comprising the steps of:

adding a diagnostic report about said pathological examination to said data in said electronic file structure at said second location; and sending said electronic file structure from said second location to said first location after said adding step is carried out.

7. The method according to claim 1 wherein said images represent a standard suite of images of the lesion.

8. The method according to claim 2 further comprising the steps of:

performing said producing, generating images, generating location information, and storing steps at a first location;

sending said electronic file structure from said first location to a second location; and receiving and storing said electronic file structure at said second location.

9. The method according to claim 8 further comprising the step of;

performing at said second location a pathological examination of said lesion in accordance with said data in said received electronic file structure.

10. The method according to claim 9 further comprising the steps of:

adding a diagnostic report about said pathological examination to said data in said electronic file structure at said second location; and sending said electronic file structure from said second location to said first location after said adding step is carried out.

11. The method according to claim 2 wherein said images represent a standard suite of images of the lesion.

12. The apparatus according to claim 3 wherein said computer system represents a first computer system, and said apparatus further comprises:

a second computer system;

means for sending said electronic file structure from said first computer system to said second computer system; and said second computer system further comprises means for receiving and storing said electronic file structure.

13. The apparatus according to claim 12 wherein said second computer system further comprises means for viewing images responsive to said data stored in said electronic file structure to assist in the pathological examination of said lesion.

14. The apparatus according to claim 13 wherein said second computer system further comprises:

means for adding a diagnostic report about the pathological examination to said data in said electronic file structure; and means for sending said electronic file structure from said second computer system to said first computer system.

15. The apparatus according to claim 3 wherein said images represent a standard suite of images of the lesion.

* * * * *